(12) United States Patent
Zhang

(10) Patent No.: US 7,714,149 B2
(45) Date of Patent: May 11, 2010

(54) CHIRAL SPIRO COMPOUNDS AND THEIR USE IN ASYMMETRIC CATALYTIC REACTIONS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 1202 days.

(21) Appl. No.: 11/218,105

(22) Filed: Sep. 1, 2005

(65) Prior Publication Data

US 2006/0047128 A1 Mar. 2, 2006

Related U.S. Application Data

(60) Provisional application No. 60/606,556, filed on Sep. 2, 2004.

(51) Int. Cl.
C07F 9/6571 (2006.01)
C07F 9/655 (2006.01)
C07D 493/10 (2006.01)

(52) U.S. Cl. .............................. 549/220; 549/5; 549/26; 549/344

(58) Field of Classification Search ................... 549/26, 549/344, 5, 220
See application file for complete search history.

(56) References Cited

FOREIGN PATENT DOCUMENTS

JP 2002265938 9/2002

OTHER PUBLICATIONS

Zhand et al. "Highly Enantioselective Copper-Catalyzed Conjugate Addition of Diethylzin to Cyclic Enones with Spirocyclic Phosphoramidite Ligands". Tetrahedron Letters. Sep. 2005, vol. 46 No. 36, pp. 6087-6090.
Wu et al. "Synthesis of New Monodentate Spiro Phosphoramidite Ligand and its Application in Ph-Catalyzed Asymmetric Hyrogenation Reaction". Organic Letters. Sep. 2004, vol. 6 No. 20, pp. 3565-7060.

PCT International Search Report dated Jun. 14, 2006 in respect to corresponding PCT Application No. PCT/US05/31341 file Sep. 1, 2005.

*Primary Examiner*—Bernard Dentz
*Assistant Examiner*—David E Gallis
(74) *Attorney, Agent, or Firm*—Ohlandt, Greeley, Ruggiero & Perle, L.L.P.

(57) ABSTRACT

The present invention provides a chiral ligand, represented by a formula or its enantiomer:

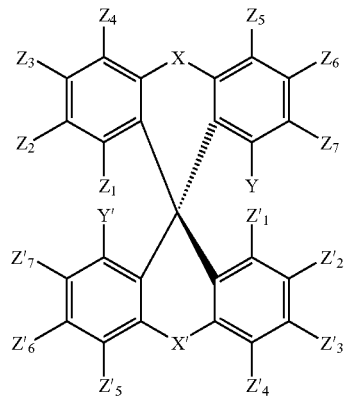

X and X' can be independently O, NH, NR, NCOR or S; each of $Z_1$-$Z_7$ and $Z_1'$-$Z_7'$ can be independently H, alkyl, aryl, substituted alkyl, substituted aryl, alkoxyl, aryloxyl, nitro, amide, aryoxide, halide, hydroxyl, carboxylate, hetereoaryl, or a cyclic alkene, fused aryl, or cyclic ether group formed from any two adjacent Z groups or any two adjacent Z' groups; Y and Y' can be independently OH, OR, $NH_2$, NHR, $NR_2$, SH, $PR_2$, $OPR_2$, $NHPR_2$, $OP(OR)_2$, COOH, COOR, CONHR, or a linking group formed from Y and Y' groups together. Processes of preparing these ligands, catalysts that employ them and methods of using the catalysts are also provided.

9 Claims, No Drawings

CHIRAL SPIRO COMPOUNDS AND THEIR USE IN ASYMMETRIC CATALYTIC REACTIONS

CROSS-REFERENCE TO RELATED PATENTS

This application claims priority from U.S. Provisional Application Ser. No. 60/606,556, filed Sep. 2, 2004.

STATEMENT REGARDING FEDERALLY SPONSORED RESEARCH AND DEVELOPMENT

This invention was made with government support under Grant No. GM058832, awarded by The National Institutes of Health. The Government has certain rights in the invention.

BACKGROUND OF THE INVENTION

1. Field of the Invention

The present invention relates to novel chiral ligands derived from new spiro compounds and their utilities in catalysts for applications in asymmetric catalysis. More particularly, the present invention relates to metal complexes of these chiral spiro ligands. The metal complexes according to the present invention are useful as catalysts in asymmetric reactions, such as hydrogenation, hydride transfer, allylic alkylation, alkylation, hydrosilylation, hydroboration, hydrovinylation, hydroformylation, olefin metathesis, hydrocarboxylation, Epoxidation, isomerization, cyclopropanation, Diels-Alder reaction, Heck reaction, isomerization, Aldol reaction, Michael addition; Mannich reaction, epoxidation, kinetic resolution, [m+n] cycloaddition and chiral Lewis acid catalyzed reactions.

2. Description of Related Art

Discovery of new chiral ligands sets the foundation of highly enantioselective transition metal-catalyzed reactions. Many chiral ligands have been developed for asymmetric catalysis, however, only few chiral ligands or motifs are suitable for the synthesis of chiral molecules in industry and academic lab. Transition-metal catalyzed enantioselective hydrogenation is a powerful strategy to synthesize chiral substances from unsaturated starting materials. Since DIOP ligand was discovered by Kagan in 1971 (Kagan, H. B.; Dang, T.-P. *Chem. Commun.* 1971, 481. (b) Kagan, H. B.; Dang, T.-P. *J. Am. Chem. Soc.* 1972, 94, 6429), a large number of bidentate ligands, especially those diphosphine ligands with $C_2$-symmetry, have been developed for highly efficient asymmetric hydrogenation of various olefins, ketones, and imines. In comparison, monodentate ligands had been much less successful due to due to the conformational flexibility of their metal/ligand complexes. However, recent advances, indicated that monodentate ligands can be effective for asymmetric hydrogenation. For example, MonoPhos has been prepared from BINOL) (Claver, C.; Fernandez, E.; Gillon, A.; Heslop, K.; Hyett, D. J.; Martorell, A.; Orpen, A. G.; Pringle, P. G. *Chem. Commun.* 2000, 961. Reetz, M. T.; Mehler, G. *Angew. Chem., Int. Ed. Engl.* 2000, 39, 3889, Hua, Z.; Vassar, V. C.; Ojima, I. *Org. Lett.* 2003, 5, 3831, Hulst, R.; de Vries, K.; Feringa, B. L. *Tetrahedron: Asymmetry* 1994, 5, 699. Berg, M. v. d.; Minnaard, A. J.; Schudde, E. P.; Esch, J. v.; Vries, A. H. M. d.; Vries, J. G. d.; Feringa, B. L. *J. Am. Chem. Soc.* 2000, 122, 11539. Pen, D.; Minnaard, A. J.; Vries, J. G. d.; Feringa, B. L. *J. Am. Chem. Soc.* 2002, 124, 14552). Excellent enantioselectivities in Rh-catalyzed asymmetric hydrogenation of α-, β-dehydroamino acid derivatives, itaconic acid derivatives, and enamides. Using 1,1-spirobiindane-7,7-diol (Birman, V. B.; Rheingold, A. L.; Lam, K.-C. *Tetrahedron: Asymmetry* 1999, 10, 125), Zhou et. al. have prepared a series of spiro monodentate phosphoramidite ligands (SIPHOS), and good to excellent results (Fu, Y.; Xie, J.-H.; Hu, A.-G.; Zhou, H.; Wang, L.-X.; Zhou, Q.-L. *Chem. Commun.* 2002, 480. Hu, A.-G.; Fu, Y.; Xie, J.-H.; Zhou, H.; Wang, L.-X.; Zhou, Q.-L. *Angew. Chem. Int. Ed.* 2002, 41, 2348. Zhu, S.-F.; Fu, Y.; Xie, J.-H.; Liu, B.; Xing, L.; Zhou, Q.-L. *Tetrahedron: Asymmetry* 2003, 14, 3219. Fu, Y.; Guo, X.-X.; Zhu, S.-F.; Hu, A.-G.; Xie, J.-H.; Zhou, Q.-L. *J. Org. Chem.* 2004, 69, 4648) have been achieved in asymmetric hydrogenation reactions (FIG. 1). Despite this success, the method for making this spirodiol is too long and tedious and the application of these ligands and catalysts are limited.

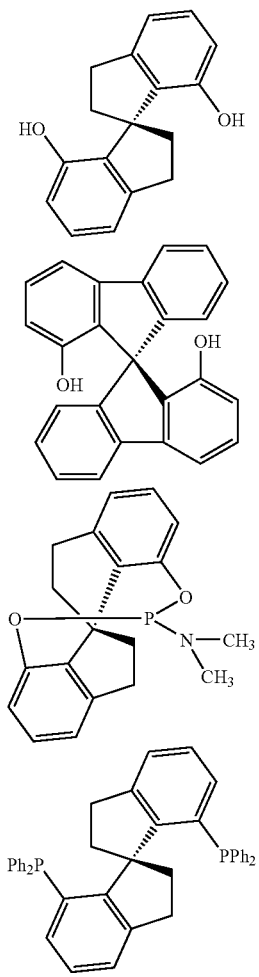

Figure 1, Prior Art

In searching for new structural motifs, we found that 9,9'-spirobixanthene was first synthesized in the 1930s (Clarkson, R. G.; Gomberg, M. *J. Am. Chem. Soc.* 1930, 52, 2881), and no further attempts had been made to assemble functional groups onto its aromatic rings. We therefore modified this spirocyclic framework into a new $C_2$-symmetrical 9,9'-spirobixanthene-1,1'-diol (FIG. 2), which possesses larger biting angle and more rigid coordinating structure than BINOL. This new spirocyclic diol (A) is among the most accessible (in one case with only two-step synthesis) diols reported to date and can be made practically for many applications.

Figure 2 Examples

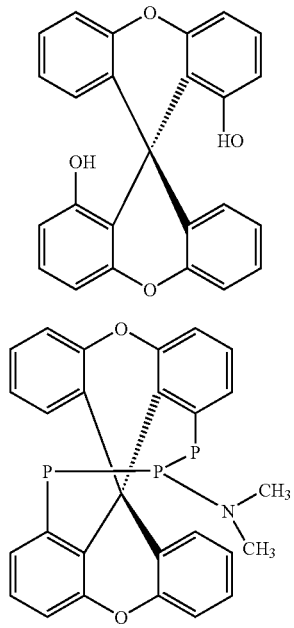

A

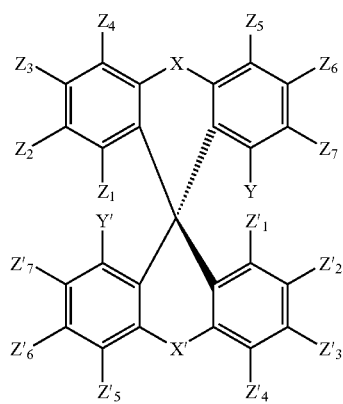

B

To demonstrate its potential role in asymmetric catalysis, spiro monodentate phosphoramidite ligand (B) (FIG. 2) was prepared, which exhibited excellent enantioselectivity (up to 99% ee) in Rh-catalyzed asymmetric hydrogenation of α-dehydroamino acid derivatives and itaconic acid.

SUMMARY OF THE INVENTION

The present invention provides a compound represented by the formula or its enantiomer:

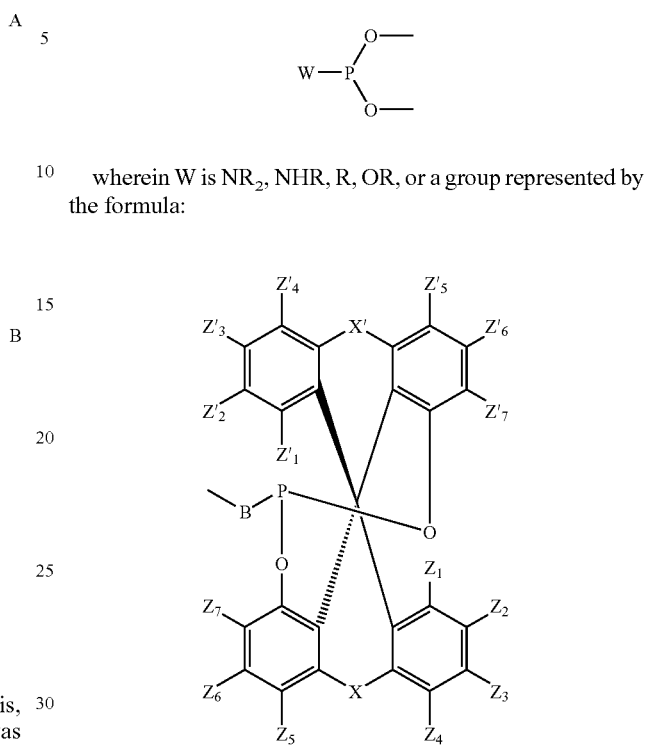

wherein X and X' are independently O, NH, NR, NCOR or S;

wherein each of $Z_1$-$Z_7$ and $Z_1'$-$Z_7'$ can be independently H, alkyl, aryl, substituted alkyl, substituted aryl, alkoxyl, aryloxyl, nitro, amide, aryoxide, halide, hydroxyl, carboxylate, hetereoaryl, or a cyclic alkene, fused aryl, or cyclic ether group formed from any two adjacent Z groups or any two adjacent Z' groups;

wherein Y and Y' are independently OH, OR, $NH_2$, NHR, $NR_2$, SH, $PR_2$, $OPR_2$, $NHPR_2$, $OP(OR)_2$, COOH, COOR, CONHR, or a linking group formed from Y and Y' groups together and represented by the formula:

$$W-P\begin{matrix}O-\\O-\end{matrix}$$

wherein W is $NR_2$, NHR, R, OR, or a group represented by the formula:

wherein B is a divalent group can be $(CH_2)_n$ wherein n is an integer from 1 to 6, 1,3-divalent phenyl, 2,2'-divalent-1,2'-biphenyl, 2,2'-divalent-1,1'biphenyl, 2,2'-divalent-1,1'-binaphthyl, ferrocene, or a substituted derivative thereof having one or more substituents each can be independently a linear, branched or cyclic alkyl of 1-8 carbon atoms, aryl of 4-10 carbon atoms, F, Cl, Br, I, COOR, $SO_3R$, hydroxy, OR, thiol, SR, aryloxyl, nitro, phosphine, and $NR_2$; and wherein each R is independently selected from the group: a linear, branched or cyclic alkyl of 1-8 carbon atoms, substituted alkyl, aryl of 4-10 carbon atoms, substituted aryl, aralkyl, and alkaryl, each R group optionally having one or more stereogenic centers.

The present invention further provides a catalyst catalyst prepared by a process including: contacting a transition metal, a salt thereof, or a complex thereof, and a ligand of the present invention wherein the contacting is carried out under reaction conditions sufficient to produce the catalyst.

The present invention still further provides a process for preparation of an asymmetric compound. The process includes the step of contacting a substrate capable of forming an asymmetric product by an asymmetric reaction and a catalyst prepared by a process including: contacting a transition metal, a salt thereof, or a complex thereof, and a ligand of the present invention, wherein the asymmetric reaction is can be hydrogenation, hydride transfer, allylic alkylation, hydrosilylation, hydroboration, hydrovinylation, hydroformylation, olefin metathesis, hydrocarboxylation, isomerization, cyclopropanation, Diels-Alder reaction, Heck reaction, isomerization, Aldol reaction, Michael addition, epoxidation, kinetic resolution and [m+n] cycloaddition wherein m=3 to 6 and n=2.

The present invention further still provides a process for preparation of a spirobixanthenonediol ligand represented by the following formula:

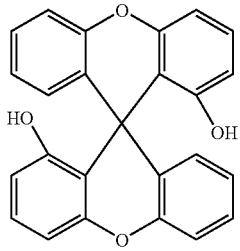

or a ring-substituted derivative thereof, the process including the steps of:

contacting a compound represented by the following formula:

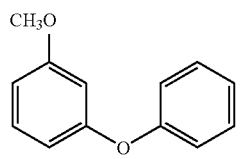

or a ring-substituted derivative thereof with n-BuLi and thereafter with a compound represented by the following formula:

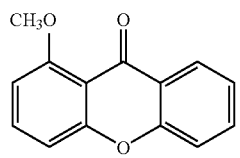

wherein the contacting is carried out at a temperature and length of time sufficient to produce a xanthenol compound represented by the following formula:

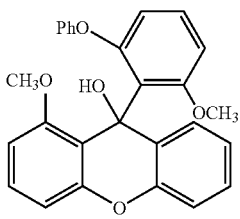

or a ring-substituted derivative thereof;

contacting the xanthenol compound or a ring-substituted derivative thereof and a mixture of concentrated hydrochloric acid and acetic acid at a temperature and length of time sufficient to produce a dimethoxy spirobixanthene compound of the following formula:

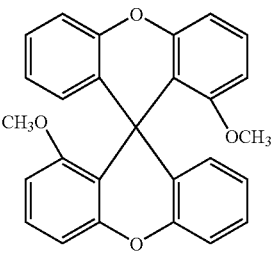

or a ring-substituted derivative thereof;

contacting the dimethoxy spirobixanthene compound or a ring-substituted derivative thereof and pyridine hydrochloride at a temperature and length of time sufficient to produce the spirobixanthenonediol compound.

The present invention further still provides a second process for the preparation of the above spirobixanthenonediol ligand or a ring-substituted derivative thereof. The process includes the steps of:

contacting a compound represented by the following formula:

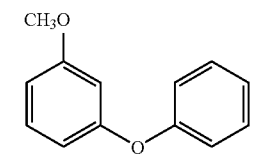

or a ring-substituted derivative thereof with n-BuLi and thereafter with an alkyl chloroformat at a temperature and length of time sufficient to produce a bis(2-methoxy-6-phenoxyphenyl)methanone compound represented by the following formula:

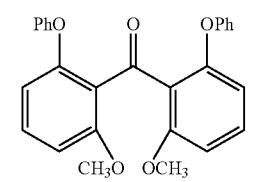

or a ring-substituted derivative thereof; and contacting the bis(2-methoxy-6-phenoxyphenyl)methanone compound or a ring-substituted derivative thereof and aluminum chloride and thereafter with concentrated hydrochloric acid at a temperature and length of time sufficient to produce the spirobixanthenonediol compound.

DETAILED DESCRIPTION OF THE INVENTION

The preferred ligand compositions according to the present invention are shown below:

Figure 3 Ligand Invention

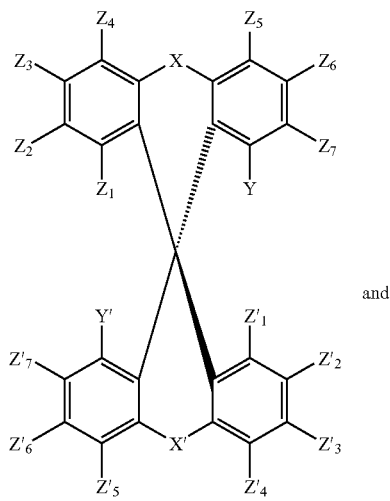

and

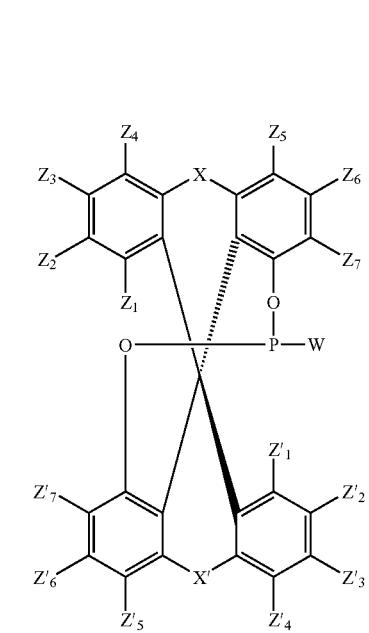

In these ligands, the bridge group X and X' for these ligands is O, NH, NR, NCOR and S, and R is an alkyl, aryl, substituted alkyl and aryl group. $Z_1$-$Z_7$ and $Z_1'$-$Z_7'$ are independently, H, alkyl, aryl, substituted alkyl, substituted aryl, alkoxyl, aryloxyl, nitro, amide, aryoxide, halide, hydroxyl, carboxylate, hetereoaryl, or linked as a cyclic alkene, extended aryl group, and cyclic ether. Y and Y' are independently, OH, OR, $NH_2$, NHR, $NR_2$, SH, $PR_2$, $OPR_2$, $NHPR_2$, $OP(OR)_2$, COOH, COOR, CONHR where R and R' are alkyl, aryl, substituted alkyl, substituted aryl or linked together as a biaryl group. In one case, W are NR2, NHR, R, OR, where R is an alkyl, aryl, substituted alkyl, substituted aryl, and these groups can have one or more stereogenic centers.

In another case, W is as follows:

W=
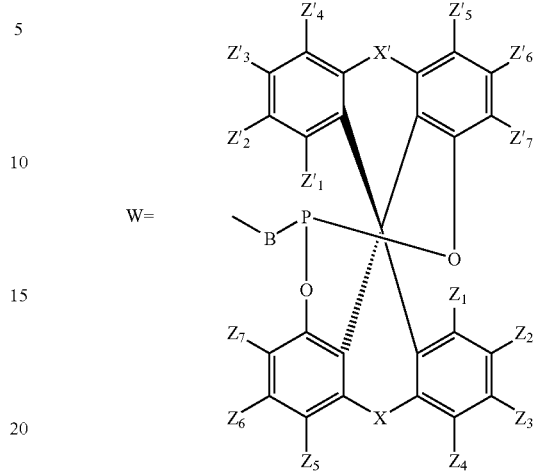

wherein B is (CH2)n where n is an integer ranging from 1 to 6, B is a divalent group selected from the group 1,3-divalent phenyl, 2,2'-divalent 1,2'-biphenyl, 2,2'-divalent-1,1'biphenyl, ferrocene, and a substituted derivative thereof; wherein each is selected from group: aryl, alkyl having 1-8 carbon atoms, F, Cl, Br, I, COOR, SO3R, OR, SR, aryloxyl, nitro, NR2 and combination thereof, wherein each R is independently selected from the group: alkyl, aryl, alkaryl and aralkyl.

Two pathways for making these types of compounds are listed below. A key element is that X, Y or X', Y' both serves as ortho directing group to remove the proton in the aromatic ring between X and Y or X' and Y'. Some of these groups include O, OR, S, POR2, NCOR, NR, NR2, COOR, and CONR2.

Figure 4, General Synthesis Pathways

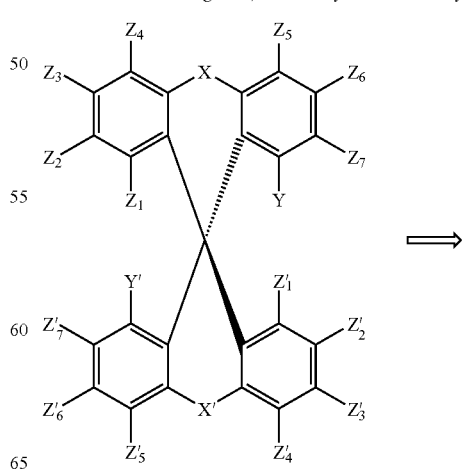

⇒

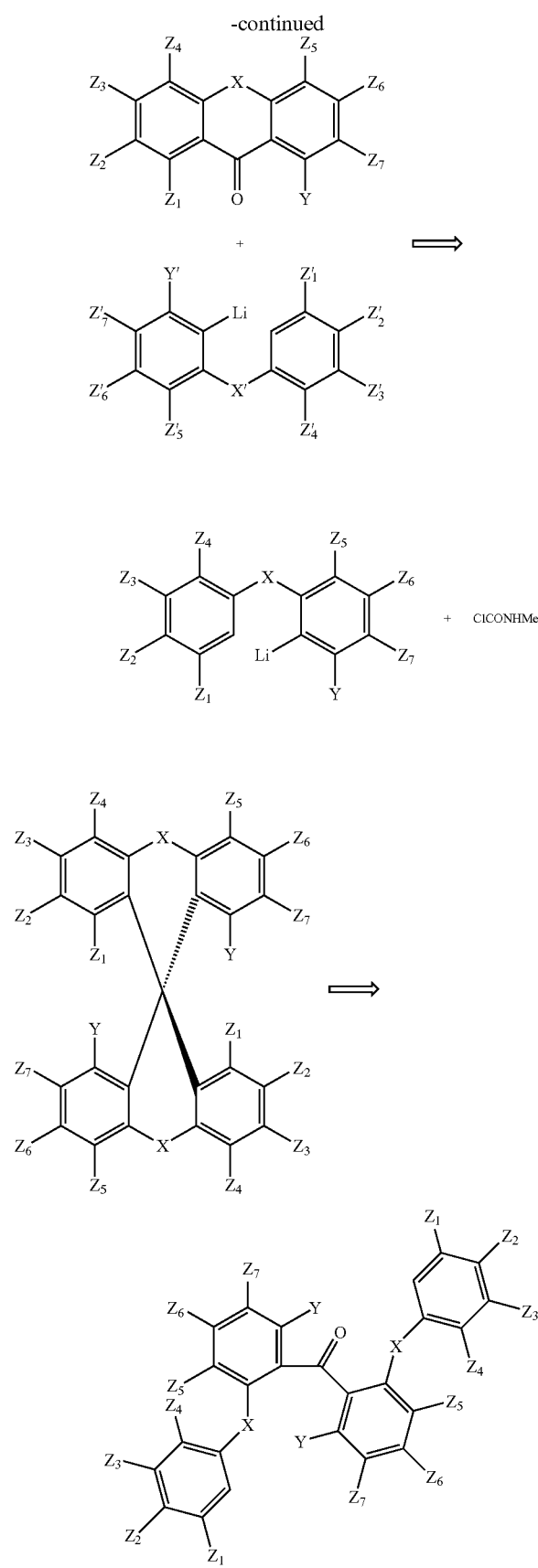

Chiral ligands having either enantiomers of ligands and a structure selected from the group:

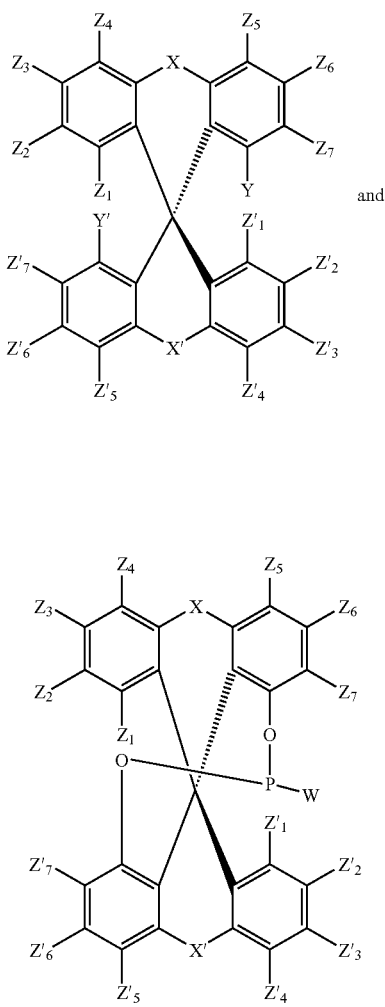

In these ligands, the bridge group X and X' for these ligands is O, NH, NR, NCOR and S, and R is an alkyl, aryl, substituted alkyl and aryl group. $Z_1$-$Z_7$ and $Z_1'$-$Z_7'$ are independently, H, alkyl, aryl, substituted alkyl, substituted aryl, alkoxyl, aryloxyl, nitro, amide, aryoxide, halide, carboxylate, hydroxyl, hetereoaryl, or linked as a cyclic alkene, extended aryl group, and cyclic ether. Y and Y' are independently, OH, OR, $NH_2$, NHR, $NR_2$, SH, $PR_2$, $OPR_2$, $NHPR_2$, $OP(OR)_2$, COOH, COOR, CONHR where R and R' are alkyl, aryl, substituted alkyl, substituted aryl or linked together as a biaryl group. In one case, W are $NR_2$, NHR, R, OR, where R is an alkyl, aryl, substituted alkyl, substituted aryl, and these groups can have one or more stereogenic centers. In another case, W is as follows:

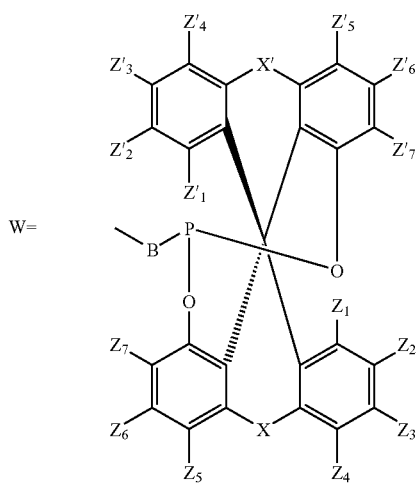

W= wherein B is (CH2)n where n is an integer ranging from 1 to 6, B is a divalent group selected from the group: 1,3-divalent phenyl, 2,2'-divalent 1,2'-biphenyl, 2,2'-divalent-1,1'biphenyl, ferrocene, and a substituted derivative thereof; wherein each is selected from group: aryl, alkyl having 1-8 carbon atoms, F, Cl, Br, I, COOR, SO3R, OR, SR, aryloxyl, nitro, NR2 and combination thereof, wherein each R is independently selected from the group: alkyl, aryl, alkaryl and aralkyl.

In a preferred embodiment, the ligand above has following structure and its enantiomer

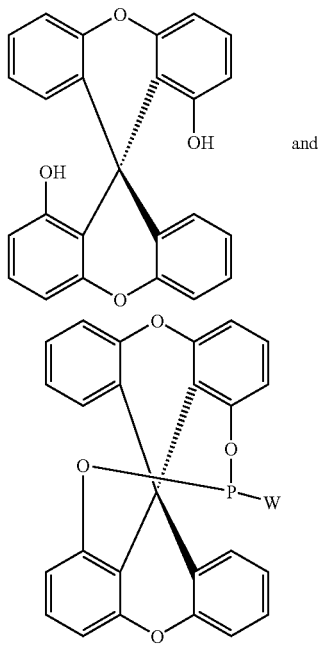

and and W is NR2, NHR, R, OR, where R is an alkyl, aryl, substituted alkyl, substituted aryl, and these groups can have one or more stereogenic centers. Specially, W is Me, Et, CH2Ph, tBu, 2,6-dimethylphenyl, OCH3, OPh, 2,6-dimethylphenoxide, NMe2, NEt2, N(i-Pr)$_2$, N(CH(CH3)Ph)2, NH(CH(CH3)Ph), N(CH3)(CH2Ph).

The process for making chiral spiro ligands though two pathways of racemic synthesis and resolution method. In this system, X, Y or X', Y' both serves as ortho directing group to remove the proton in the aromatic ring between X and Y or X' and Y'. Some of these groups include O, OR, S, POR2, NCOR, NR, NR2, COOR, and CONR2.

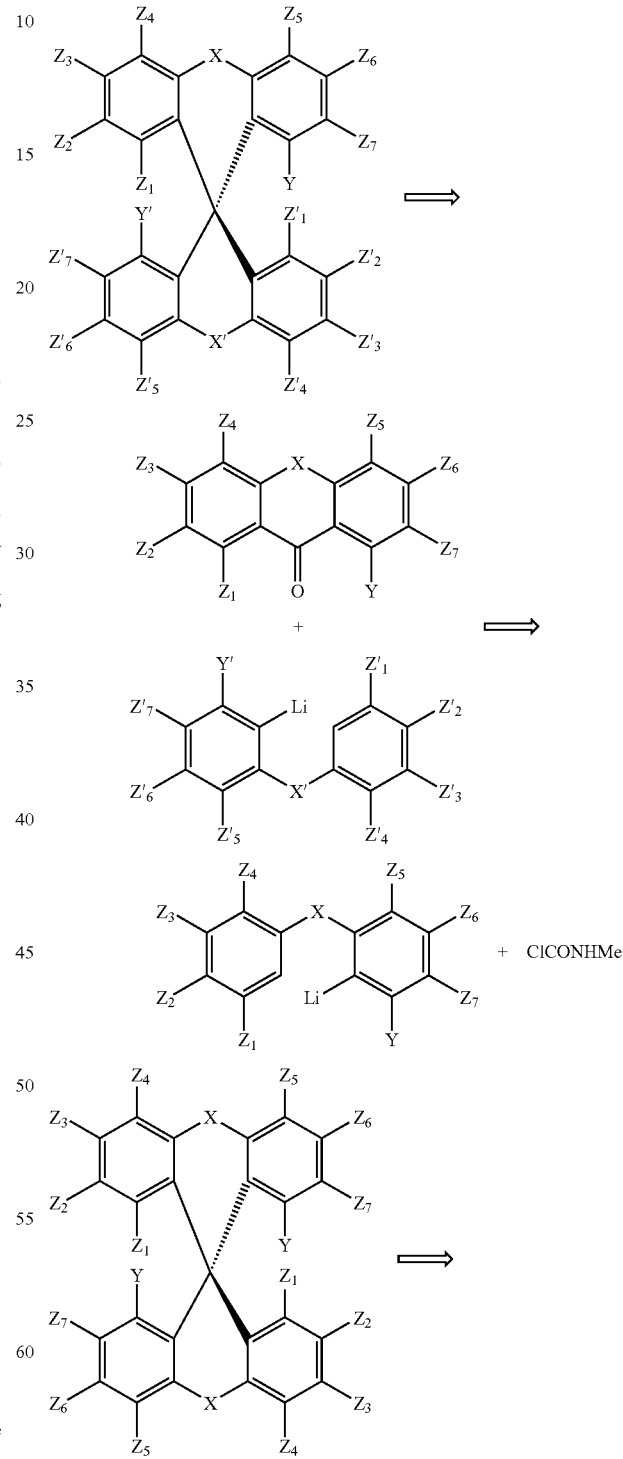

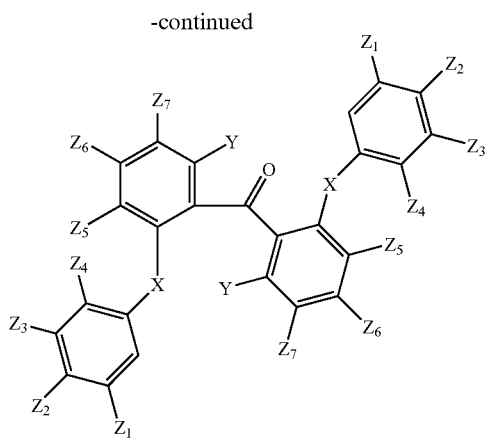

Catalysts can be prepared with the ligands above with metals selected from the group: Cu, Ag, Au, Ni, Pt, Pd, Rh, Ru and Ir where ligands with at least phosphorus atom.

The transition metal salt, or complex thereof, is selected from the group: AgX; Ag(OTf); Ag(OTf)$_2$; AgOAc; PtCl$_2$; H$_2$PtCl$_4$; Pd$_2$(DBA)$_3$; Pd(OAc)$_2$; PdCl$_2$(RCN)$_2$; (Pd(allyl)Cl)$_2$; Pd(PR$_3$)$_4$; (Rh(NBD)$_2$)X; (Rh(NBD)Cl)$_2$; (Rh(COD)Cl)$_2$; (Rh(COD)$_2$)X; Rh(acac)(CO)$_2$; Rh(ethylene)$_2$(acac); (Rh(ethylene)$_2$Cl)$_2$; RhCl(PPh$_3$)$_3$; Rh(CO)$_2$Cl$_2$; RuHX(L)$_2$(diphosphine), RuX$_2$(L)$_2$(diphosphine), Ru(arene)X$_2$(diphosphine), Ru(aryl group)X$_2$; Ru(RCOO)$_2$(diphosphine); Ru(methallyl)$_2$(diphosphine); Ru(aryl group)X$_2$(PPh$_3$)$_3$; Ru(COD)(COT); Ru(COD)(COT)X; RuX$_2$(cymen); Ru(COD)$_n$; Ru(aryl group)X$_2$(diphosphine); RuCl$_2$(COD); (Ru(COD)$_2$)X; RuX$_2$(diphosphine); RuCl$_2$(=CHR)(PR'$_3$)$_2$; Ru(ArH)Cl$_2$; Ru(COD)(methallyl)$_2$; (Ir (NBD)$_2$Cl)$_2$; (Ir(NBD)$_2$)X; (Ir(COD)$_2$Cl)$_2$; (Ir(COD)$_2$)X; CuX(NCCH$_3$)$_4$; Cu(OTf); Cu(OTf)$_2$; Cu(Ar)X; CuX; Ni(acac)$_2$; NiX$_2$; (Ni(allyl)X)$_2$; Ni(COD)$_2$; MnX$_2$ and Mn(acac)$_2$; wherein each R and R' is independently selected from the group: alkyl or aryl; Ar is an aryl group; and X is a counter-anion.

Rh-catalysts with ligands with at least one phosphorus atom are suitable for hydrogenation olefins, imines, enamides and ketones.

The catalyst and catalyst precursor can be [Rh(COD)Cl]$_2$, [Rh(COD)$_2$]X (X=BF$_4$, ClO$_4$, SbF$_6$, CF$_3$SO$_3$, BAr$_4$ etc), [Ir(COD)Cl]$_2$, [Ir(COD)$_2$]X (X=BF$_4$, ClO$_4$, SbF$_6$, CF$_3$SO$_3$, etc) and chiral ligand with at least one phosphorus atom. The catalysts can be Ru(RCOO)$_2$(diphosphine), RuX$_2$(diphosphine) (X=Cl, Br, I), Ru(methylallyl)$_2$(diphosphine), Ru(aryl group)X$_2$(diphosphine) and other Ru catalysts with chiral ligands with at least one phosphorus atom.

The catalyst precursor can be [Rh(COD)Cl]$_2$, [Rh(COD)$_2$]X (X=BF$_4$, ClO$_4$, SbF$_6$, CF$_3$SO$_3$, BAr$_4$ etc), [Ir(COD)Cl]$_2$, [Ir(COD)$_2$]X (X=BF$_4$, ClO$_4$, SbF$_6$, CF$_3$SO$_3$, etc) and catalyst can be formed from catalyst precursor and chiral ligands of the present invention such as those with at least one phosphorus atom.

The catalysts can be Ru(RCOO)$_2$(diphosphine), RuX$_2$(diphosphine) (X=Cl, Br, I), Ru(methylallyl)$_2$(diphosphine), Ru(aryl group)X$_2$(diphosphine) and other Ru catalysts with chiral ligands with at least one phosphorus atom.

Catalyst with ligands of the present invention and transition metals, such as, rhodium, iridium, ruthenium, and palladium are used for asymmetric hydrogenation of ketones, imines, enamides and olefins.

The transition metal catalyzed asymmetric reactions with the catalysts of the present invention include hydrogenation, hydride transfer reaction, hydrosilylation, hydroboration, hydrovinylation, hydroformylation, hydrocarboxylation, allylic alkylation, cyclopropanation, Diels-Alder reaction, Aldol reaction, Heck reaction and Michael addition.

Rh, Ru, Ir, Pd compounds of the chiral ligands with at least one phosphorus atom are preferred.

The preferred catalysts are formed from [Rh(COD)Cl]$_2$, [Rh(COD)$_2$]X (X=BF$_4$, ClO$_4$, SbF$_6$, CF$_3$SO$_3$, etc), [Ir(COD)Cl]$_2$, [Ir(COD)$_2$]X (X=BF$_4$, ClO$_4$, SbF$_6$, CF$_3$SO$_3$, etc), Rh(acac)(CO)$_2$, Ni(ally)X (X=BF$_4$, ClO$_4$, SbF$_6$, CF$_3$SO$_3$, etc), Pd$_2$(dba)$_3$, [Pd(allyl)Cl]2, and chiral ligands with at least one phosphorus atom.

Chiral Lewis acid catalysts with ligands with chiral diols are also preferred. The Lewis acid element can be Ti, Zr, Hf, Mg, Ca, B, Al, La-group elements, Ga, Mo, V, Li, Zn, Cu.

The catalyst precursor of Lewis acid compounds with the diols include Ti(OR)4, TiCl4, AlR3, AlCl3, Ti(Cl)2(OR), Zr(OR)4, MoO2(acac), VO(acac)2, La(OTf)3, La(OAc)3, Cu(OTf)2, n-BuLi, BH3, NaBH4, LiAlH4, BMe3, ZnEt2, MoNR(CHR)(OR)2, Mo(CO)6.

Such catalysts can be used for asymmetric alkylation, Diels-Alder reaction, olefin metathesis, epoxidation, aldol reaction, Mannich reactions, Michael addition and allylic alkylation.

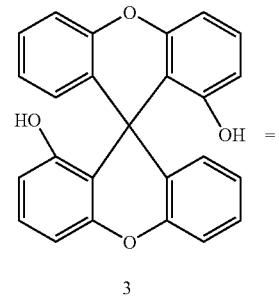

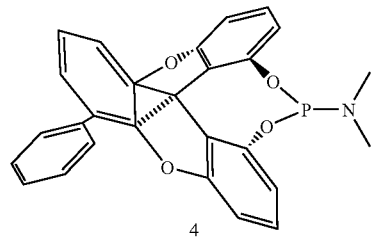

9,9'-spirobixanthene-1,1'-diol (3) and its Phosphoramidate Compound (4)

Considering the C$_2$ symmetric structure of 3, we envisioned double cyclization of ketone would be one of efficient approaches.

Among the two possible ways (Scheme 1) to disconnect the spirocyclic backbone into its ketone precursor, method a requires protection with removable substituents of the positions para to the methoxy groups in the aromatic ring before cyclization occurs.

On the other hand, there is no competing cyclization in method b. Therefore, it is a preferred strategy to construct the designed spirocyclic molecule.

Scheme 1. Retro synthetic analysis of 3.

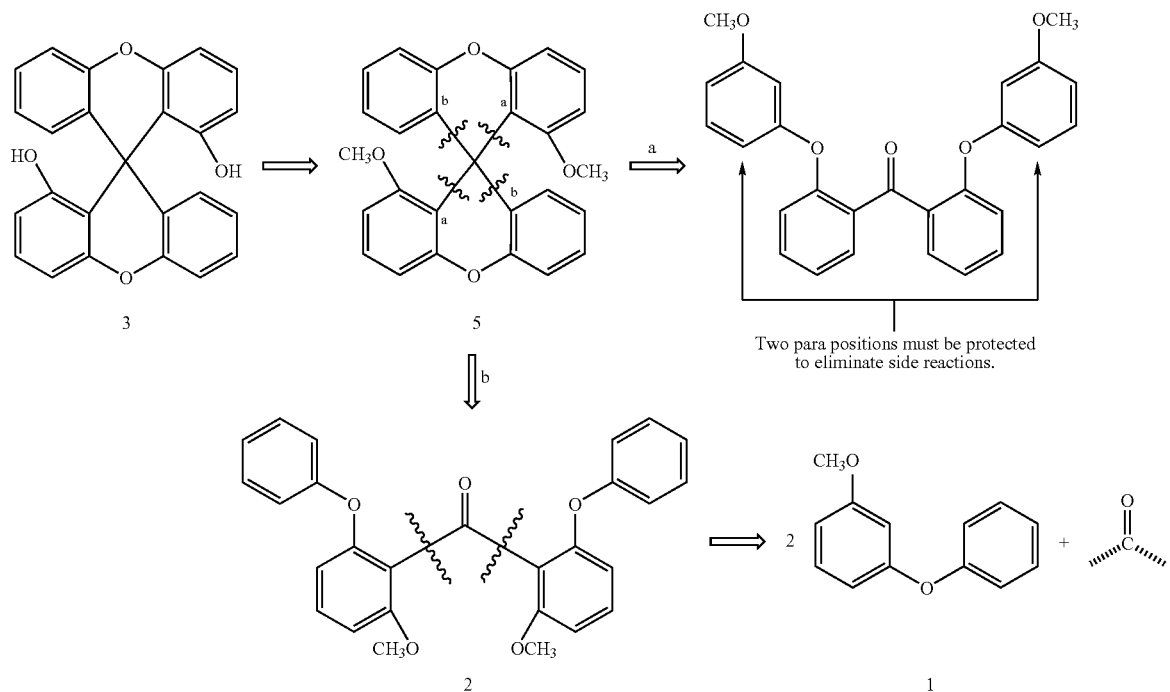

Starting from 3-phenoxyanisole (1), the symmetric ketone 2 was prepared in a moderate yield by linking two equivalents of lithiated 1 with methyl chloroformate (Scheme 2). Following treatment of 2 with an acid was expected to produce the spiran precursor 5. However, several acidic reagents ($H_2SO_4$, HCl, polyphosphoric acid, acetic acid, and trifluoroacetic acid) have been tested, and none of them can lead to the desired product. Interestingly, when we tried $AlCl_3$, target molecule 3 was formed directly.

As a Lewis acid, $AlCl_3$ can promote not only Friedel-Craft alkylation but also deprotection of methyl ether. That accounts for the direct formation of 3 from 2 in one pot.

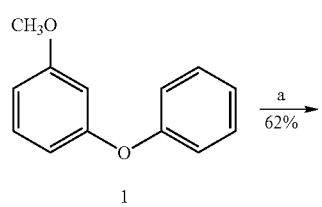

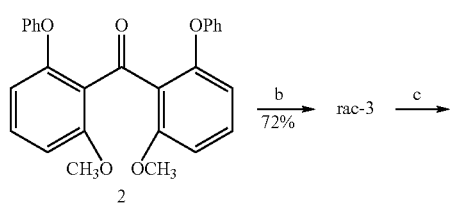

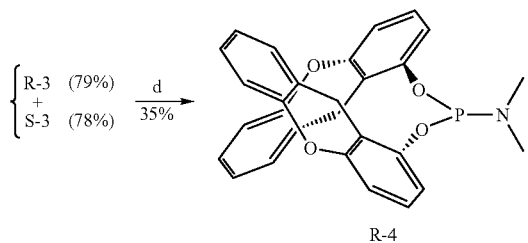

Reagents and conditions: (a) (i) n-BuLi, THF, −78° C., (ii) $ClCO_2CH_3$, THF, −78° C.; (b) (i) $AlCl_3$, toluene, reflux, (ii) conc. HCl, reflux; (c) (i) N-benzylcinchonidinium chloride, acetonitrile; (ii) N-benzylquininium chloride, acetonitrile; (d) hexamethylphosphorous triamide, toluene, reflux.

To obtain enantiomerically pure 3, co-crystallization of racemic 3 with chiral resolving reagents has been extensively studied. The most efficient reagent was found to be N-benzylcinchonidinium chloride (6), which can precipitate as co-crystals with one enantiomer of 3 in acetonitrile. X-ray diffraction of a single crystal grown from the precipitate revealed a regularly packed molecular complex of 3 and 6 in 1:1 molar ratio. Based on the crystal structure of 6, the absolute configuration of 3 is assigned to be (R). The other (S) enantiomer of 3 can be obtained from the mother solution by co-crystallization with N-benzylquininium chloride.

To make a clear presentation, some chiral ligands with this characteristics are listed. For each class of ligands, the corresponding enantiomer is also included.

These selective examples are used to illustrate the new chiral spiro compounds (L1-L41). These compounds can be prepared and used for asymmetric catalytic reactions (FIG. 5-8).
Figure 5. Examples
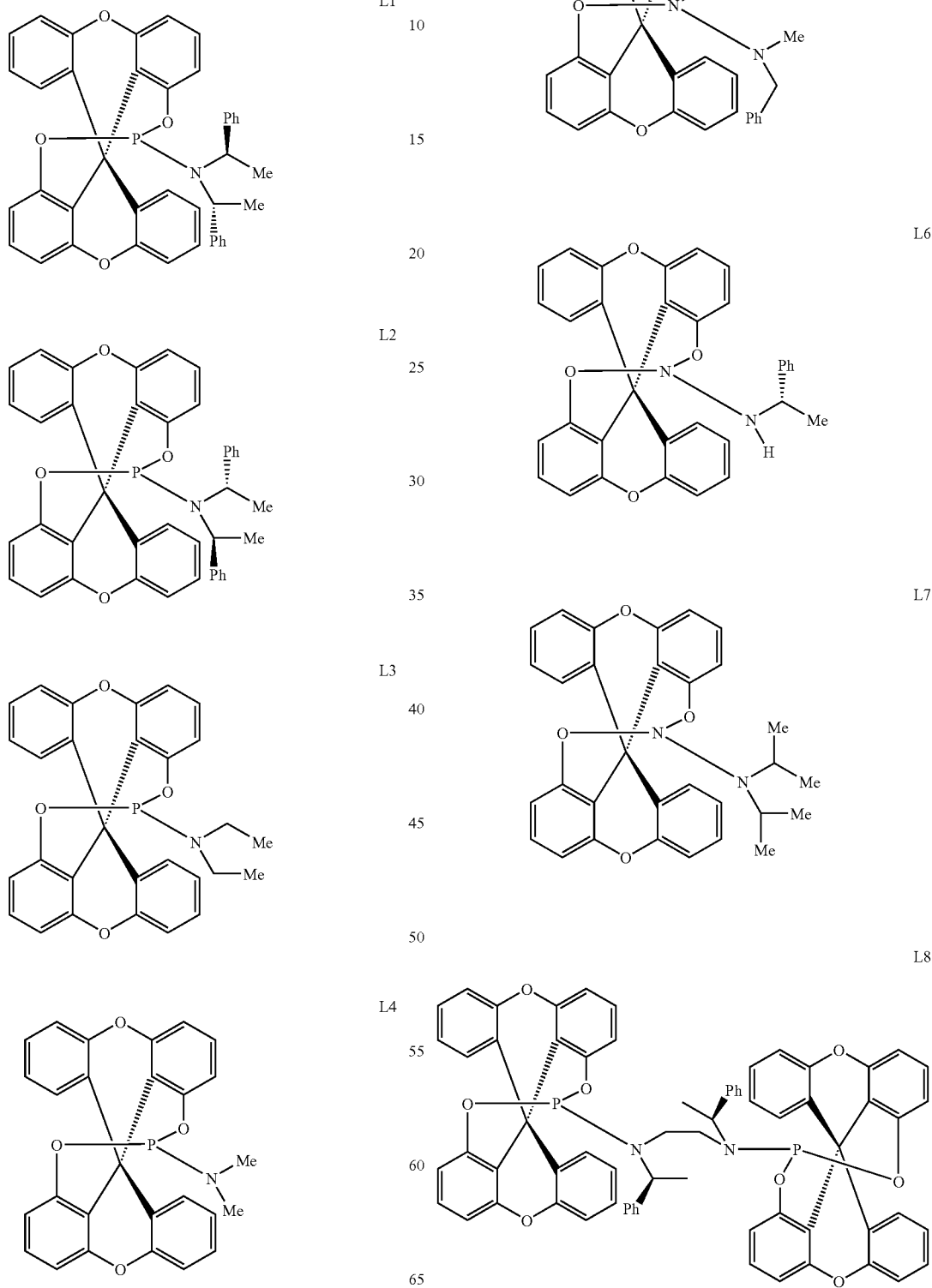

Figure 6. Examples
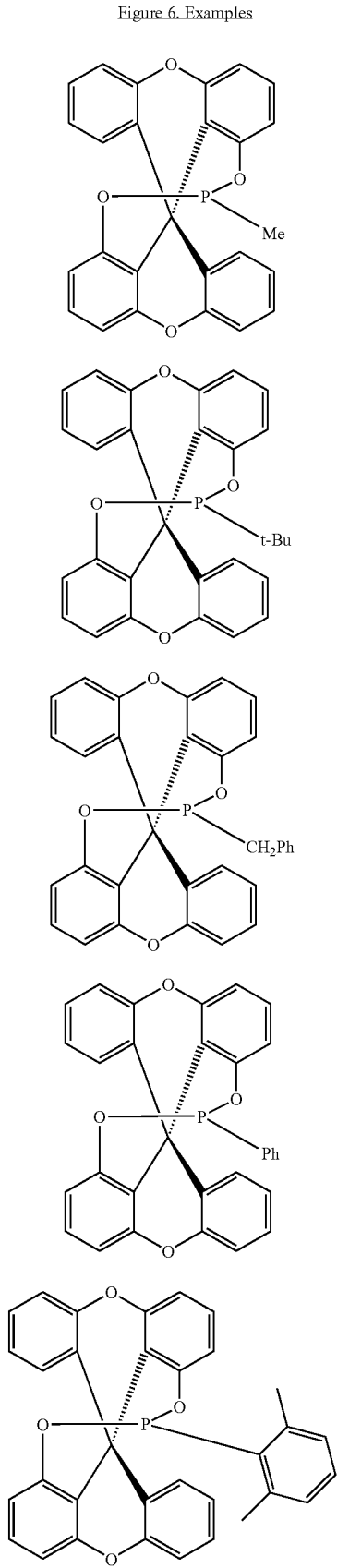
L8
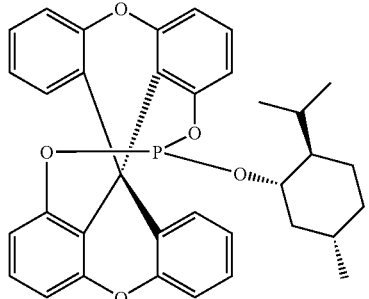
L9
L10
L11
L12
-continued
L13
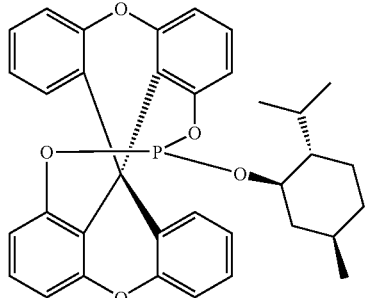
L14
L15
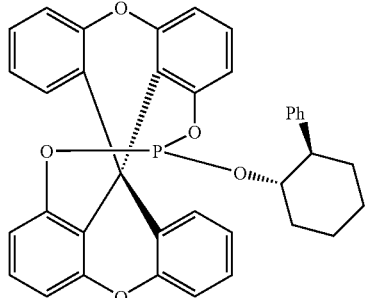
L16
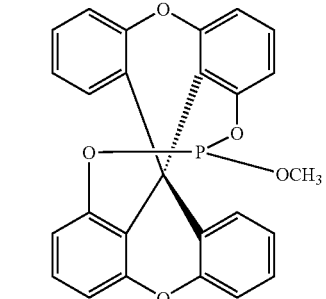
L17
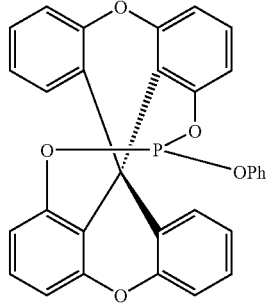

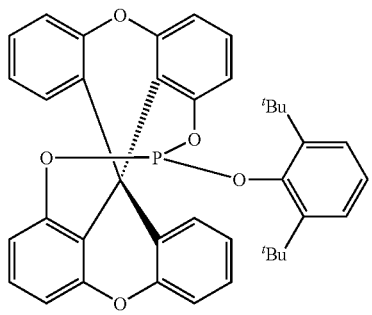
L18
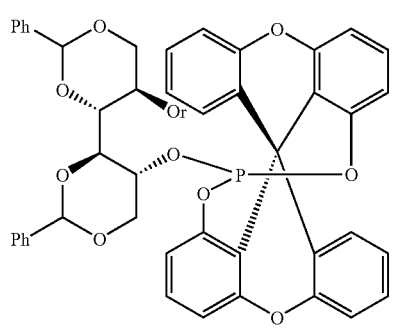
L19
Figure 7. Examples
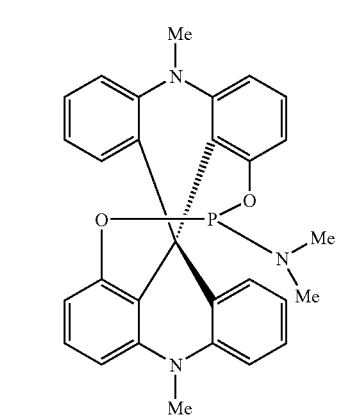
L20
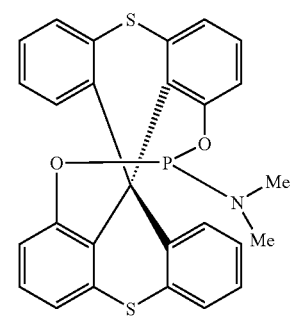
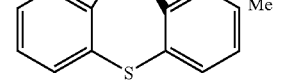
L21
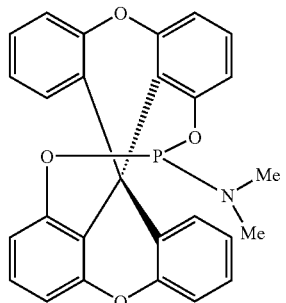
L22
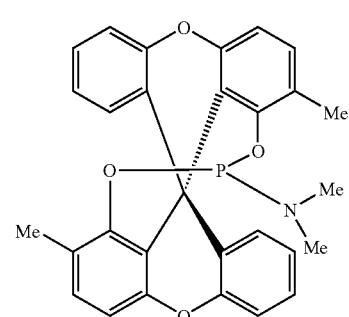
L23
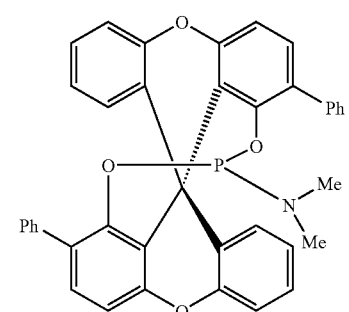
L24
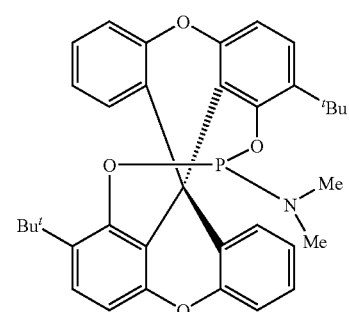
L25
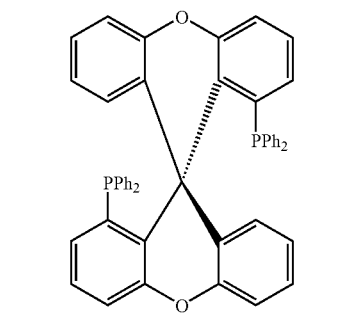
L26

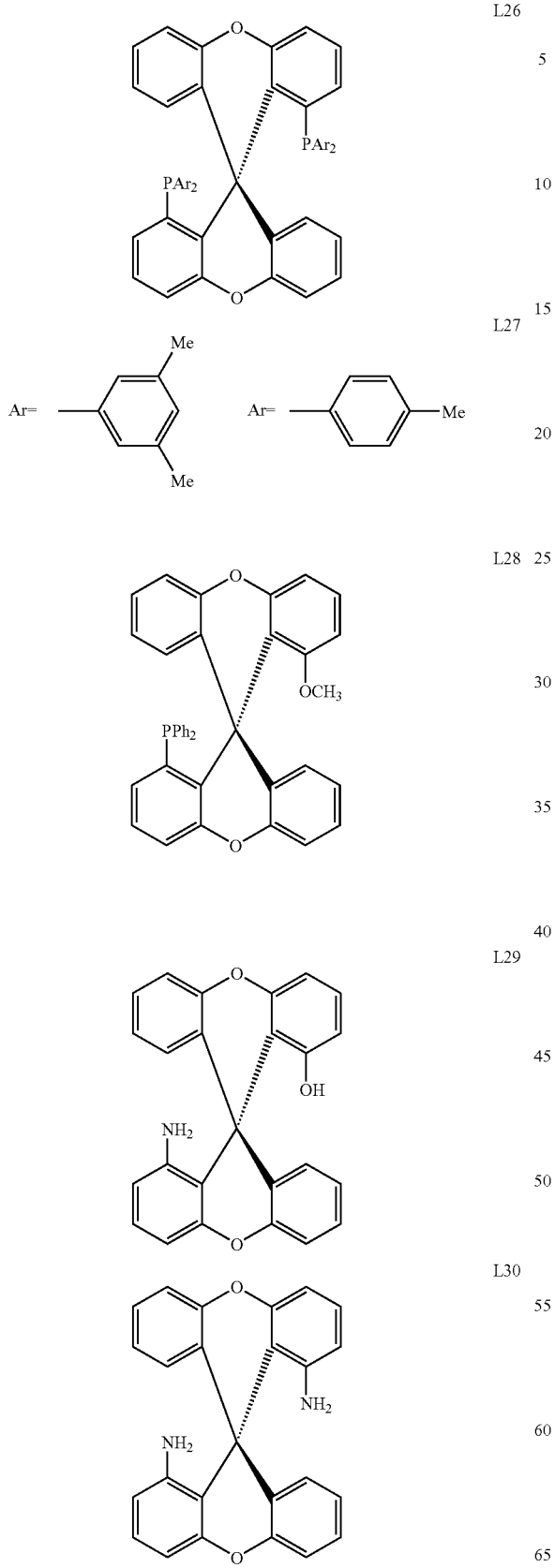
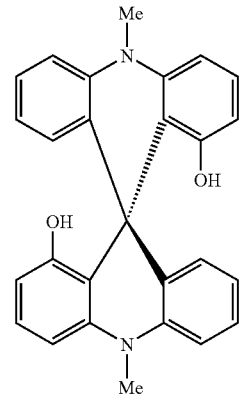
Figure 8. Examples
L31
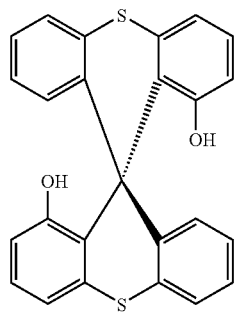
L32
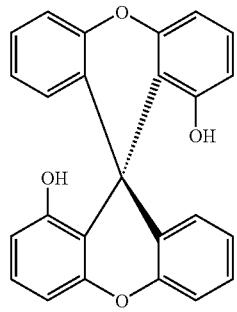
L33
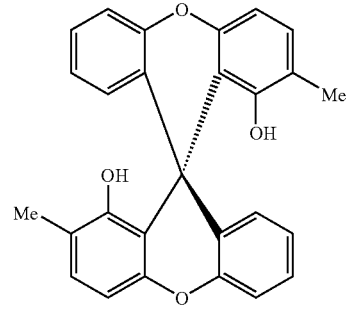
L34

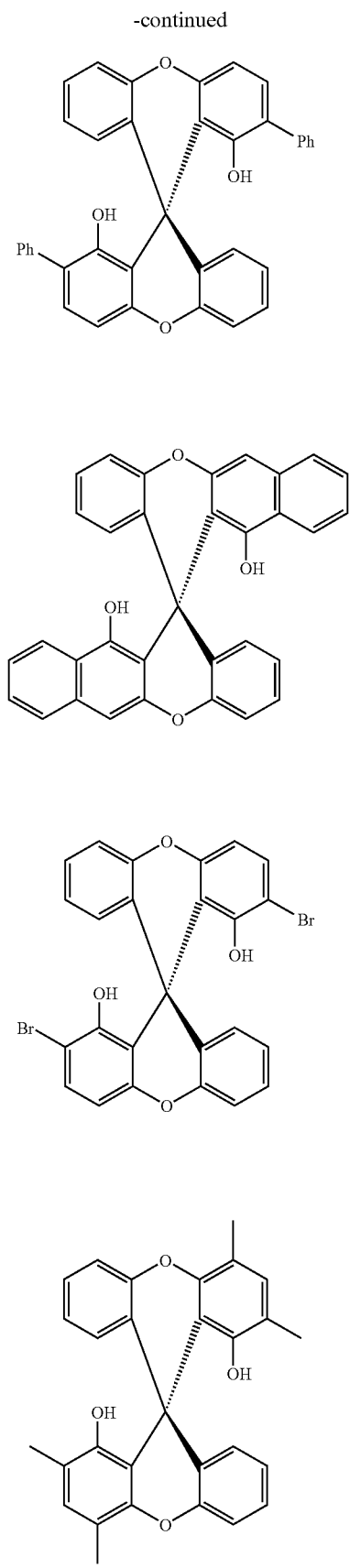

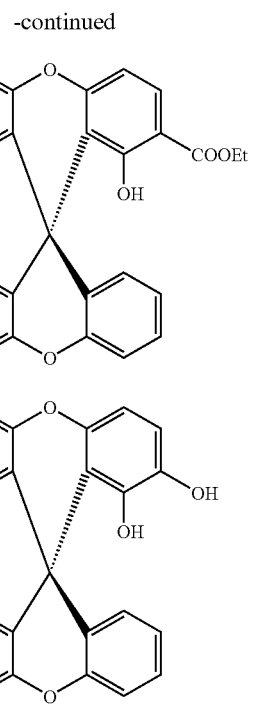

General Procedures

All reactions and manipulations were performed in a nitrogen-filled glovebox or using standard Schlenk techniques. THF and toluene were dried and distilled from sodium-benzophenone ketyl under nitrogen. Methylene chloride was distilled from $CaH_2$. Methanol was distilled from Mg under nitrogen. (R,R)-BDNPB was made a solution of 10 mg/ml in toluene before use.

Column chromatography was performed using EM silica gel 60 (230–400 mesh).

$^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard.

Optical rotation was obtained on a Perkin-Elmer 241 polarimeter. MS spectra were recorded on a KRATOS mass spectrometer MS 9/50 for LR-EI and HR-EI.

GC analysis was carried on Hewlett-Packard 6890 gas chromatography using chiral capillary columns.

HPLC analysis was carried on Waters™ 600 chromatography.

Ligand Synthesis (Pathway I)w

1-Methoxy-3-Phenoxybenzene (a)

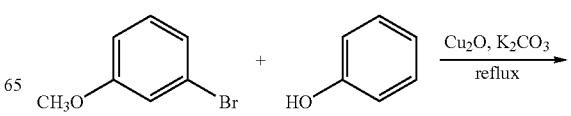

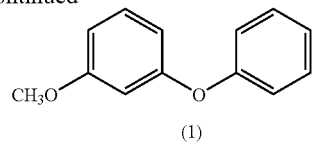

(1)

3-bromoanisole (470 g, 2.51 mol), phenol (292 g, 3.08 mol), copper (I) oxide (548 g, 3.83 mol), and potassium carbonate (190 g, 1.37 mol) were refluxed with mechanic stirring at 190° C. for one hour, then cooled down. A small amount of phenol (50 g, 0.53 mol) was added, and then refluxed for 3 hours and 30 minutes, and then cooled down to room temperature.

$CH_2Cl_2$ (1.5 L) was added into the reaction system, and stirred for 1 hour. The mixture was passed through a short Celite plug to remove insoluble substances. The residue on the plug was further washed with $CH_2Cl_2$ (700 mL×3). The combined organic phase was washed with 2N NaOH (120 g in 1.5 L water), brine (500 mL×2), dried over $Na_2SO_4$, and concentrated. Distillation under reduced pressure afforded the product as colorless liquid (440 g, yield 88%).

1-Methoxyxanthen-9-One (b)

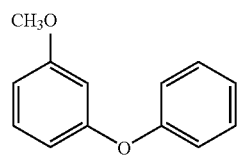

1. n-BuLi, -78° C.
2. $Me_2NCOCl$, -78° C.
3. LDA, 0° C.

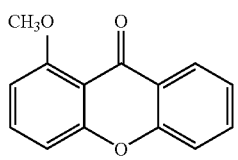

To the solution of a (246 g, 1.23 mol) in THF (1000 mL) was added n-BuLi (2.5 M, 507 mL, 1.42 mol) by a 1000 mL-dropping funnel at −78° C. in 1.5 hour. After stirring at this temperature for 1 hour, it was stirred at room temperature for 1 hour. Then it was cooled to −78° C. again, transferred via cannular into the solution of dimethylcarbamic chloride (113 mL, 1.23 mol) in THF (500 mL) at −78° C. After stirring at this temperature for 1 hour, it was stirred at room temperature for another 4 hours. Meanwhile, LDA was prepared by adding n-BuLi (2.5 M, 1200 mL) slowly into diisopropylamine (491 mL, 3.49 mol) in THF (2500 mL) at −78° C. The prepared LDA solution was then stirred at −78° C. for 15 minutes, followed by stirring at room temperature for 30 minutes. Then the intermediate solution prepared from a was added via cannular into LDA solution at 0° C., stirring overnight.

Aqueous HCl (3N, 1 L) was introduced to quench the reaction at 0° C., stirred for 30 minutes so that phase separation occurred. The two layers were separated, the organic phase washed with brine, aqueous $NaHCO_3$ (saturated), and brine. The water layer was extracted with EtOAc, washed with aqueous $NaHCO_3$ (saturated), and brine. The combined organic solution was dried over $Na_2SO_4$, concentrated. EtOAc/hexane (1:9) was used to wash out impurities and afford product as light yellow powder (248 g, yield 89%).

1-Methoxy-9-(2-Methoxy-6-Phenoxyphenyl) Xanthen-9-ol (c)

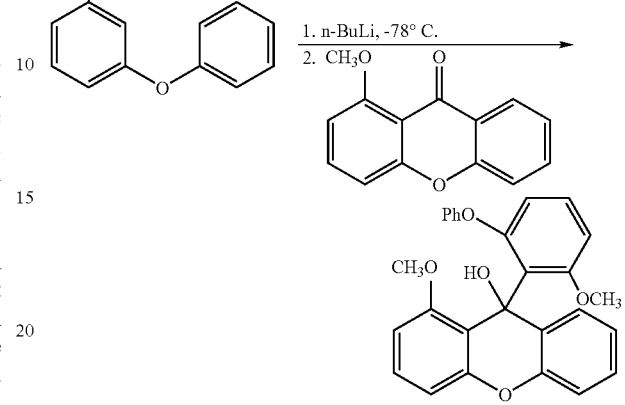

Lithiation of a (206 g, 1.03 mol) was achieved as described in step 2 (433 mL n-BuLi and 1000 mL THF was used), and the solution was then added into b (233 g) in THF (4000 mL) at −78° C. within 1 hour, stirred overnight. Saturated $NH_4Cl$ solution (1 L) was used to quench the reaction at 0° C. and a lot of solid appeared. A Celite plug was used to filter the solid.

The THF mother solution was concentrated, and the filtrate was washed with $CH_2Cl_2$ (about 3.5 L). All the organic solution was combined, dried over $Na_2SO_4$, concentrated. Acetone was used to wash out impurity, giving the desired product as white powder (347 g, yield 79%).

1,1'-Dimethoxy-9,9'-Spirobixanthene (d)

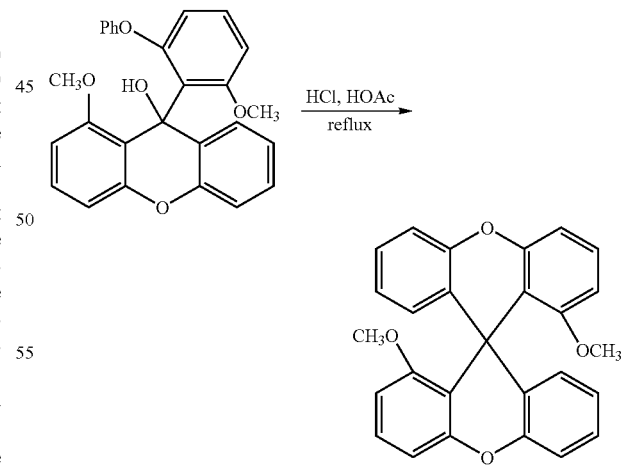

d (347 g, 0.81 mol), acetic acid (3000 mL), and concentrated HCl (2000 mL) were refluxed for 6 hours so that the original deep purple color faded to light pink. HOAc was removed under reduced pressure. The residue was dissolved in $CH_2Cl_2$ (10 L), washed with saturated $NaHCO_3$ solution, and brine, dried over $Na_2SO_4$, concentrated. Acetone (600 mL) was used to wash out impurity, giving the desired product as white powder (275 g, yield 83%).

rac-9,9'-Spirobixanthenone-1,1'-diol (e)

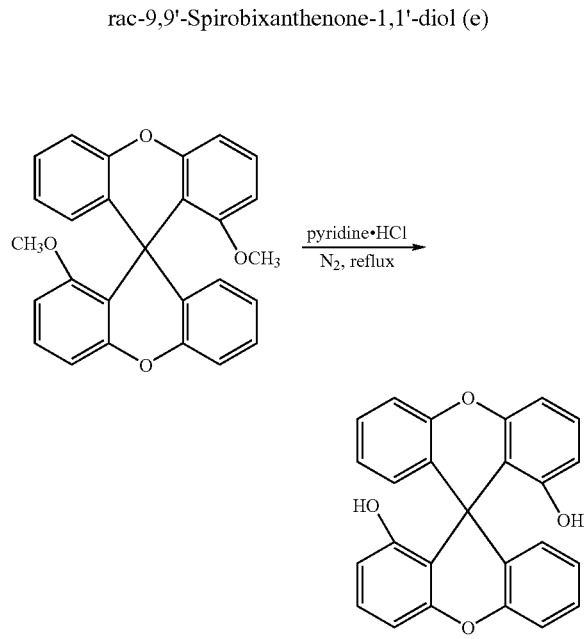

d (49 g, 0.13 mol) and pyridine.HCl (304 g, 2.63 mol) were heated to reflux for 25 minutes. The reaction mixture was diluted with HCl solution (4 N, 300 mL concentrated HCl in 600 mL water), extracted with EtOAc (1.5 L). The organic phase was further washed with HCl (4N) twice (450 mL each), then water (600 mL), saturated NaHCO₃ solution (500 mL), brine (500 mL), dried over $Na_2SO_4$. After EtOAc was removed, acetone (150 mL) was used to wash out impurity to get product as off white powder (32 g, yield 70%).

Ligand Synthesis (Path Way II)

Synthesis of chiral monodentate spiro ligand via 9,9'-spirobixanthene-1,1'-diol.

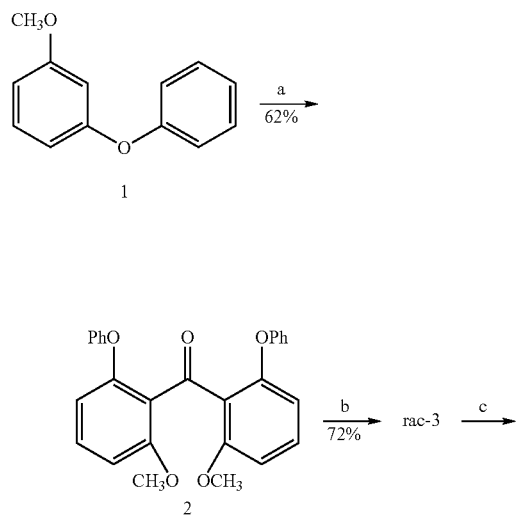

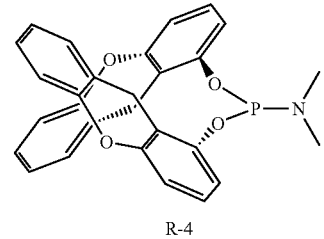

Reagents and conditions: (a) (i) n-BuLi, THF, −78° C., (ii) $ClCO_2CH_3$, THF, −78° C.; (b) (i) $AlCl_3$, toluene, reflux, (ii) conc. HCl, reflux; (c) (i) N-benzylcinchonidinium chloride, acetonitrile; (ii) N-benzylquininium chloride, acetonitrile; (d) hexamethylphosphorous triamide, toluene, reflux.

Bis(2-Methoxy-6-Phenoxyphenyl)Methanone (2)

To a solution of 1 (10.0 g, 25.0 mmol) in dry THF (80 mL) was slowly added n-BuLi (20 mL, 50 mmol, 2.5 M in hexane) at −78° C. within 15 minutes. The solution was stirred at −78° C. for 30 minutes, then at room temperature for two hours. The solution was then cooled to −78° C. again, and transferred through a cannular into the solution of methyl chloroformate (1.94 mL, 25 mmol) in dry THF (40 mL) at −78° C., then stirred overnight. The reaction was quenched by slowly adding 20 mL of aqueous $NH_4Cl$ (saturated) at 0° C. The solvent THF was then removed under reduced pressure and the residue was extracted with EtOAc. The combined organic solution was washed with water and brine, dried over $Na_2SO_4$, and concentrated. The white precipitates were collected by filtration, and dried in vacuum to get 2 (6.6 g, 62% yield). $^1$H-NMR (360 MHz, $CD_2Cl_2$) δ 3.69 (s, 6H, ArO—$CH_3$), 6.39, 6.40 (d, 2H, J=8.3 Hz, Ar—H), 6.61, 6.63 (d, 2H, J=8.3 Hz, Ar—H), 6.76-6.79 (m, 4H, Ar—H), 7.01-7.05 (m, 2H, Ar—H), 7.16-7.25 (m, 6H, Ar—H); $^{13}$C-NMR (91 MHz, $CD_2Cl_2$) δ 56.7, 107.1, 111.7, 119.1, 123.6, 124.7, 130.0, 131.7, 156.1, 157.7, 159.3, 191.9.

(±)-9,9'-Spirobixanthene-1,1'-diol (3)

To a solution of 2 (1.0 g, 2.3 mmol) in dry toluene (20 mL) was added $AlCl_3$ (1.9 g, 14.3 mmol). The solution was warmed slowly and refluxed for 30 minutes. Then it was cooled to 0° C. and concentrated aqueous HCl (20 mL) was introduced with vigorous stirring. After refluxing for 1 hour, the reaction mixture was extracted with EtOAc, washed with concentrated HCl, water, aqueous NaHCO₃ and brine, dried over $Na_2SO_4$, and concentrated. Flash chromatography (eluting with $CH_2Cl_2$) gave 3 as light-yellow powder (0.64 g, yield 72%).

$^1$H-NMR (360 MHz, $CD_2Cl_2$) δ 6.29, 6.31 (d, 2H, Ar—H), 6.59-6.61 (dd, 2H, $J_1$=8.2 Hz, $J_2$=0.9 Hz, Ar—H), 6.78-6.80 (m, 4H, Ar—H), 6.97-7.01 (m, 4H, Ar—H), 7.04-7.08 (m, 2H, Ar—H), 8.12 (s, 2H, Ar—OH); $^{13}$C-NMR (91 MHz, $CD_2Cl_2$) δ 38.5, 107.5, 111.0, 115.7, 116.6, 123.3, 127.8, 128.8, 131.7, 132.1, 150.2, 151.9, 156.7.

Resolution of (±)-9,9'-Spirobixanthene-1,1'-diol (3)

A suspension of racemic 3 (3.14 g, 8.26 mmol) and N-benzylcinchonidinium chloride 6 (1.84 g, 4.37 mmol) in acetonitrile (30 mL) was refluxed for 6 hours, then cooled slowly to room temperature overnight. The white solid (1:1 inclusion complex, 99.1% ee) was collected by filtration, then refluxed in acetonitrile (20 mL) for 6 hours, and cooled slowly to room temperature overnight. This precipitate was collected by filtration, washed twice with small amount of $CH_3CN$ and dried in vacuum.

To a suspension of the purified 1:1 complex in ethyl acetate (30 mL) was added 2N HCl (20 mL). The mixture was stirred until the entire solid was dissolved. The organic layer was separated, washed with 2N HCl (20 mL) and brine, dried over $Na_2SO_4$. Concentration under reduced pressure produced enantiomerically pure (R)-(+)-3 (1.24 g, 79% yield, >99.9% ee). $[\alpha]^{20}_D=+40.2$ (c=1.0, $CHCl_3$).

The mother solution containing enriched S enantiomer was concentrated, and refluxed with N-benzylquininium chloride (1.97 g, 4.37 mmol) in acetonitrile (30 mL) for 6 hours. The clear solution was allowed to cool overnight. The precipitate was collected by filtration, washed with small amount of acetonitrile. Then it was added into EtOAc, washed with 2N HCl and brine, dried over $Na_2SO_4$. Concentration under reduced pressure produced enantiomerically pure (S)-(−)-3 (1.22 g, 78% yield, 99.8% ee). The ee value was determined by HPLC on a Chiralcel AD-H column with isopropanol/hexane (4:96) as eluent.

(R)-O,O'-(9,9'-Spirobixanthene-1,1'-diyl)-N,N-Dimethylphosphoramide [(R)-4]

To the solution of (R)-3 (0.5 g, 1.32 mmol) in 10 mL dry toluene was added hexamethylphosphorous triamide (287 μL, 1.58 mmol). The solution was stirred at reflux for 72 hours. Then the toluene was removed under reduced pressure. Flash chromatography on silica gel with $CH_2Cl_2$ afforded (R)-4 as white powders. (0.21 g, 35%).

$^1$H-NMR (360 MHz, $CD_2Cl_2$) δ 2.29 (s, 6H, —N($CH_3$)$_2$), 6.33-6.35 (m, 1H, Ar—H), 6.43-6.45 (m, 1H, Ar—H), 6.72-6.75 (m, 1H, Ar—H), 6.84-6.89 (m, 2H, Ar—H), 7.03-7.07 (m, 2H, Ar—H), 7.11-7.15 (m, 2H, Ar—H), 7.21-7.25 (m, 2H, Ar—H), 7.39-7.48 (m, 2H, Ar—H); $^{13}$C-NMR (91 MHz, $CD_2Cl_2$) δ 35.7 (d, J=15.5 Hz, —N($CH_3$)$_2$), 43.5 (s, C), 113.4 (s, C—H), 114.1 (d, J=2.6 Hz, C—H), 117.2 (d, J=4.2 Hz, 2(C—H)), 119.9 (s, C), 121.1-121.2 (m, C—H), 121.6 (d, J=1.4 Hz, C—H), 124.2 (d, J=1.7 Hz, 2(C—H)), 126.5 (d, J=1.5 Hz, 2(C—H)), 128.3 (s, C), 128.7 (s, C—H), 128.9 (d, J=2.7 Hz, C—H), 129.7 (s, C—H), 129.9 (d, J=2.1 Hz, C—H), 148.2 (d, J=4.1 Hz, 2C), 150.3 (s, C), 150.4 (s, C), 151.6 (d, J=3.5 Hz, 2C), 155.3 (s, C), 155.4 (s, C); $^{31}$P-NMR (146 MHz, $CD_2Cl_2$) δ 123.2 (s).

General Procedure of Hydrogenation

A solution of [Rh(nbd)$_2$]BF$_4$ (0.374 mg, 0.001 mmol) and ligand (R)-3 (1.0 mg, 0.0022 mmol) in $CH_2Cl_2$ (0.5 mL) was stirred in a glove-box for 10 min to allow the catalyst precursor to form. Then it was added into the solution of substrate (0.1 mmol) in 2.5 mL of $CH_2Cl_2$. Hydrogenation was performed in an autoclave with 25 psi of $H_2$ at room temperature for 12 hours. After releasing $H_2$, the reaction mixture was passed through a short silica gel plug to remove the catalyst. The concentrated solution was used for chiral GC to measure the enantiomeric excess. For hydrogenation of itaconic acid, the ee was determined by its corresponding dimethyl ester.

TABLE 1

Rh(I)/(R)-4-catalyzed asymmetric hydrogenation of α-dehydroamino acid derivatives and itaconic acid[a]

| entry | substrate | ee (%)[b] | configuration[c] |
|---|---|---|---|
| 1[d] | R = H | 98.2 | S |
| 2 | R = Ph | 98.4 | S |
| 3 | R = p-F—Ph | 99.9 | S |
| 4 | R = p-Cl—Ph | 99.1 | S |
| 5 | R = o-Cl—Ph | 99.3 | S |
| 6 | R = m-Br—Ph | 99.8 | S |
| 7 | R = 2-naphthyl | 99.8 | S |
| 8 | (itaconic acid) 9 | 97.9[e] | S |

[a]Refer to Experimental Section for details. All hydrogenation reactions were performed with 0.1 mmol substrate and 0.0001 mmol in situ prepared [Rh(nbd)$_2$]BF$_4$(R)-4 in $CH_2Cl_2$ at room temperature, $P_{H2}$ = 25 psi. 100% conversion was observed within 12 hours.
[b]Determined by chiral GC (Chirasil-VAL III FSOT).
[c]The S absolute configuration was assigned by comparison of optical rotation with reported data.
[d]THF/$CH_2Cl_2$ (5:1) was used as solvent.
[e]The ee was measured through its corresponding methyl ester (chiral GC, Gamma Dex-225).

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A compound represented by the formula or its enantiomer:

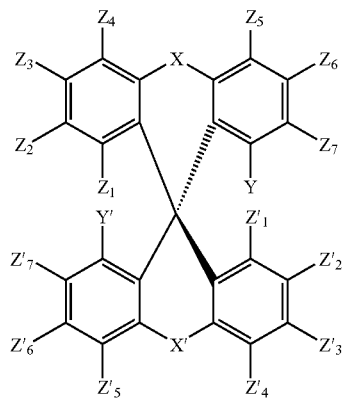

wherein X and X' are independently selected from the group consisting of: O, and S;

wherein each of $Z_1$-$Z_7$ and $Z_1'$-$Z_7'$ is independently selected from the group consisting of: H, alkyl, aryl, substituted alkyl, substituted aryl, alkoxyl, aryloxyl, nitro, amide, halide, hydroxyl, carboxylate, heteroaryl, and a cyclic alkene, fused aryl, or cyclic ether group formed from any two adjacent Z groups or any two adjacent Z' groups;

wherein Y and Y' are independently selected from the group consisting of: OH, OR, $NH_2$, NHR, $NR_2$, SH, $PR_2$, $OPR_2$, $NHPR_2$, $OP(OR)_2$, COOH, COOR, CONHR, and a linking group formed from Y and Y' groups together and represented by the formula:

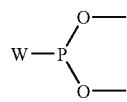

wherein W is selected from the group consisting of: $NR_2$ and NHR: and wherein each R is independently selected from the group: a linear, branched or cyclic alkyl of 1-8 carbon atoms, substituted alkyl, aryl of 4-10 carbon atoms, substituted aryl, aralkyl, and alkaryl, each R group optionally having one or more stereogenic centers.

2. The compound of claim 1, wherein said compound is a racemic mixture of enantiomers.

3. The compound of claim 1, wherein said compound is a non-racemic mixture of enantiomers.

4. The compound of claim 1, wherein said compound is one of the enantiomers.

5. The compound of claim 1, wherein said compound has an optical purity of at least 85% ee.

6. The compound of claim 1, wherein said compound has an optical purity of at least 95% ee.

7. The compound of claim 1, wherein said compound is represented by the formula or its enantiomer:

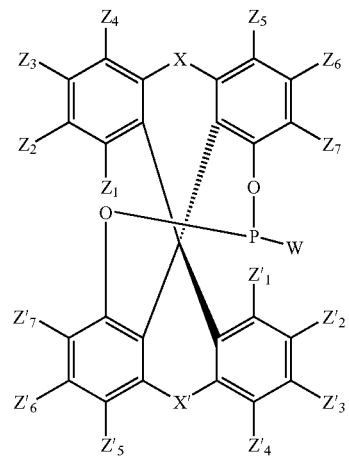

wherein X and X' are independently selected from the group consisting of: O and S;

wherein each of $Z_1$-$Z_7$ and $Z_1'$-$Z_7'$ is independently selected from the group consisting of: H, alkyl, aryl, substituted alkyl, substituted aryl, alkoxyl, aryloxyl, nitro, amide, halide, hydroxyl, carboxylate, heteroaryl, and a cyclic alkene, fused aryl, or cyclic ether group formed from any two adjacent Z groups or any two adjacent Z' groups;

wherein W is selected from the group consisting of: $NR_2$ and NHR: and wherein each R is independently selected from the group: a linear, branched or cyclic alkyl of 1-8 carbon atoms, substituted alkyl, aryl of 4-10 carbon atoms, substituted aryl, aralkyl, and alkaryl, each R group optionally having one or more stereogenic centers.

8. The compound of claim 1, wherein said compound has an optical purity of at least 85% ee.

9. The compound of claim 1, wherein said compound is represented by the following formulae or their enantiomers:

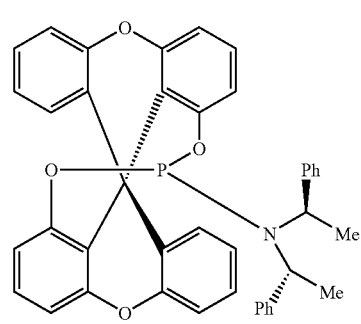

-continued
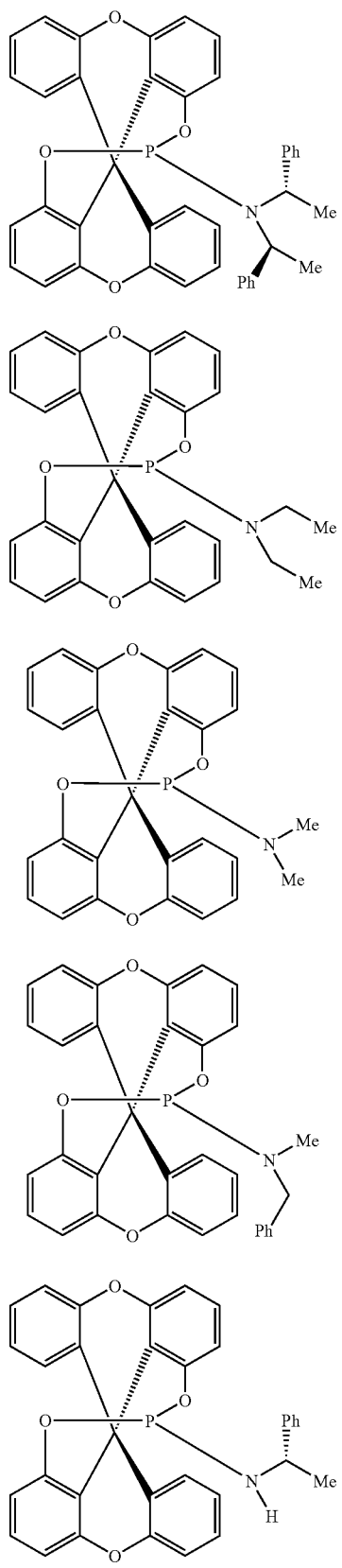
L2
L3
L4
L5
L6
-continued
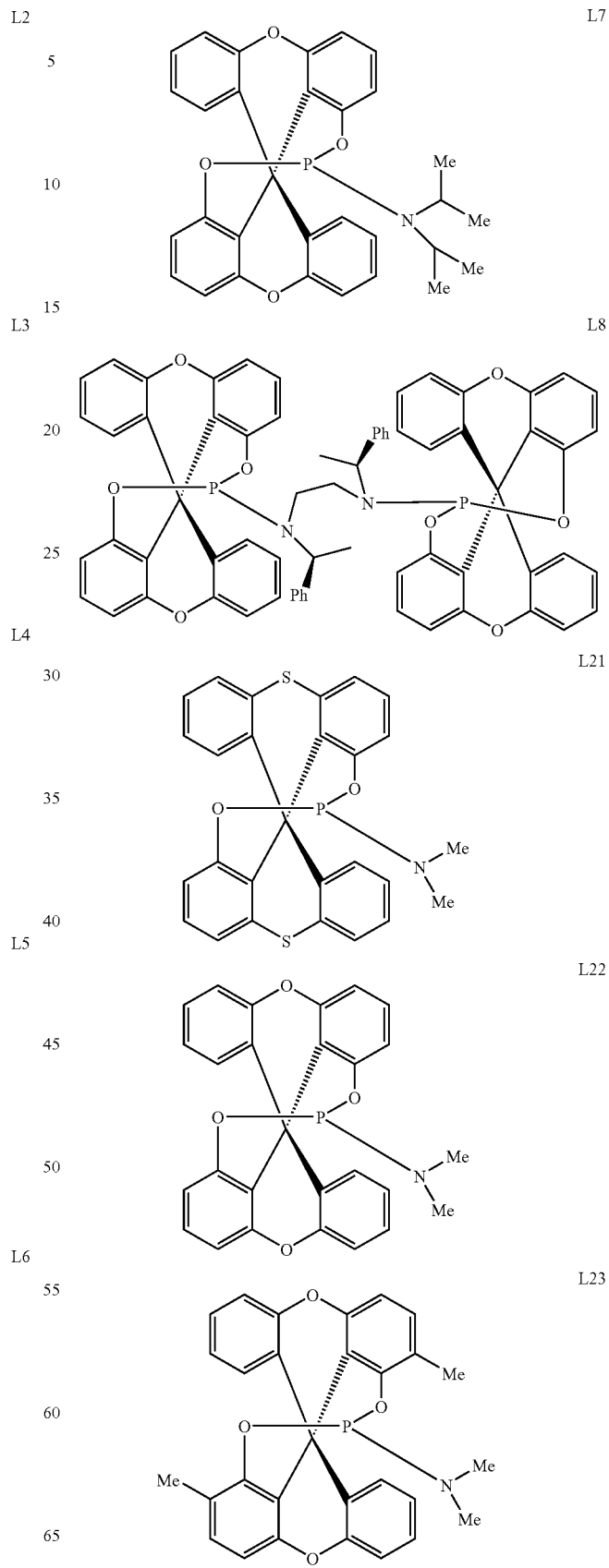
L7
L8
L21
L22
L23

-continued
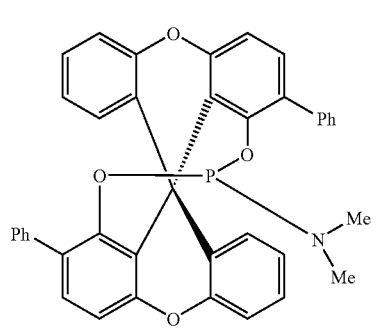
L24
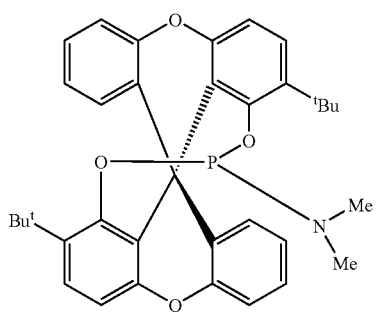
L25
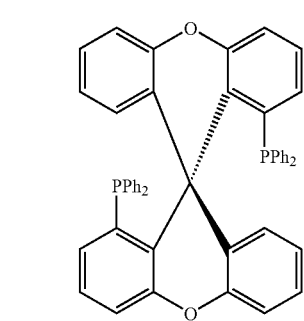
L26
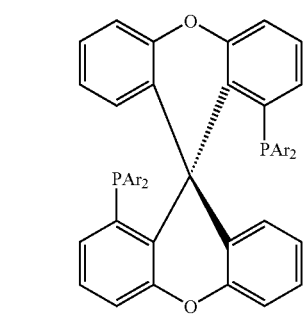
L26
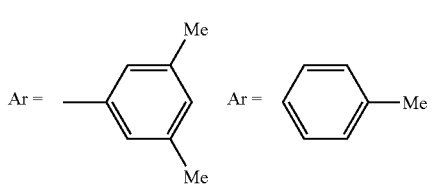
L27
-continued
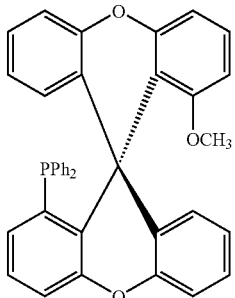
L28
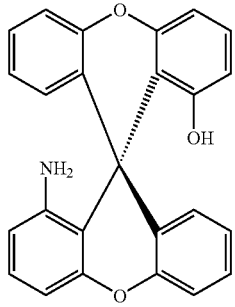
L29
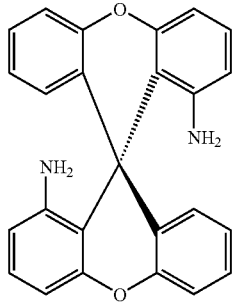
L30
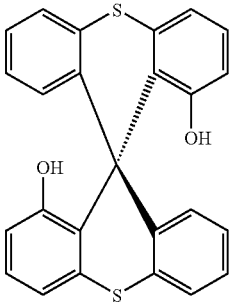
L32
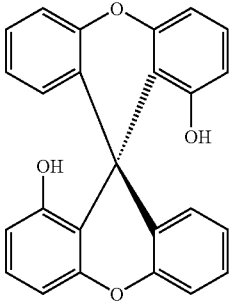
L33

-continued
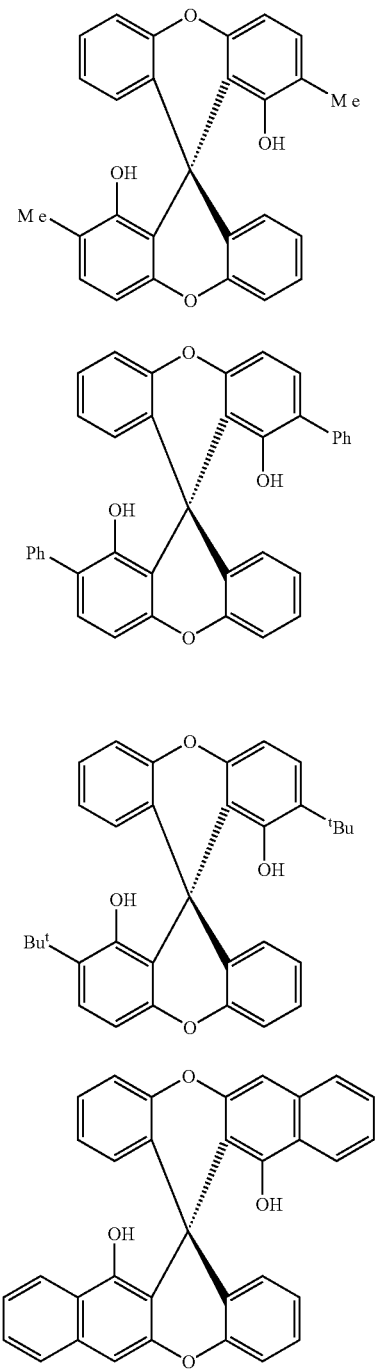
L34
L35
L36
L37
-continued
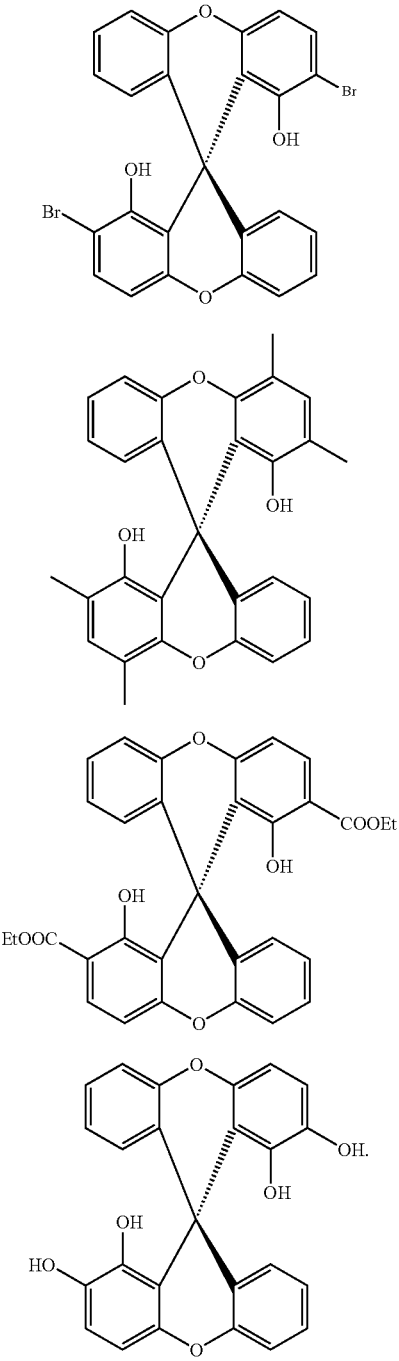
L38
L39
L40
L41
* * * * *